(12) United States Patent  
Miller

(10) Patent No.: US 12,564,652 B1  
(45) Date of Patent: Mar. 3, 2026

(54) ELEVATOR STERILIZATION SYSTEM AND METHOD OF USING SAME

(71) Applicant: Philip Glen Miller, Lake Charles, LA (US)

(72) Inventor: Philip Glen Miller, Lake Charles, LA (US)

( * ) Notice: Subject to any disclaimer, the term of this patent is extended or adjusted under 35 U.S.C. 154(b) by 1017 days.

(21) Appl. No.: 17/382,977

(22) Filed: Jul. 22, 2021

Related U.S. Application Data

(60) Provisional application No. 63/054,998, filed on Jul. 22, 2020.

(51) Int. Cl.

| | |
|---|---|
| *A61L 2/10* | (2006.01) |
| *A61L 2/24* | (2006.01) |
| *B66B 1/34* | (2006.01) |
| *B66B 3/00* | (2006.01) |
| *B66B 5/00* | (2006.01) |
| *B66B 11/02* | (2006.01) |

(52) U.S. Cl.  
CPC .................. *A61L 2/10* (2013.01); *A61L 2/24* (2013.01); *B66B 1/3484* (2013.01); *B66B 3/002* (2013.01); *B66B 5/0012* (2013.01); *B66B 11/0226* (2013.01); *A61L 2202/11* (2013.01); *A61L 2202/14* (2013.01); *A61L 2202/25* (2013.01)

(58) Field of Classification Search  
CPC .......... A61L 2/10; A61L 2/24; A61L 2202/11; A61L 2202/14; A61L 2202/25  
See application file for complete search history.

(56) References Cited

U.S. PATENT DOCUMENTS

| | | | | |
|---|---|---|---|---|
| 8,791,441 B1 * | 7/2014 | Lichtblau | .................. | A61L 2/10 |
| | | | | 250/455.11 |
| 9,666,424 B1 * | 5/2017 | Veloz | ...................... | H01J 61/52 |
| 10,857,249 B2 * | 12/2020 | Brais | ......................... | A61L 9/20 |

FOREIGN PATENT DOCUMENTS

| | | | | |
|---|---|---|---|---|
| WO | WO-0160419 A1 * | 8/2001 | ............... | A61L 2/10 |

OTHER PUBLICATIONS

Lowe, et al. N95 Filtering Facepiece Respirator Ultraviolet Germicidal Irradiation (UVGI) Process for Decontamination and Reuse. Nebraska Medicine. Apr. 10, 2020. Accessed at https://www.nebraskamed.com/sites/default/files/documents/covid-19/n-95-decon-process.pdf.

* cited by examiner

*Primary Examiner* — Sean E Conley  
(74) *Attorney, Agent, or Firm* — Brozynski & Dalton, PC; Katarzyna Brozynski; Curtis Rew

(57) ABSTRACT

An ultraviolet anti-pathogen device for an elevator car is disclosed. The device includes occupant sensors, such as motion detectors to sense movement, weight sensors to sense the presence of occupants, or head sensors to sense the presence of occupants to assure that occupants have evacuated the car prior to sterilization or sanitization. Subsequently, UV-C generators, such as a bank of mercury bulbs, generate intense levels of UV-C. An array of multiple UV-C sensors scan the car, and determine the darkest area, or the area reflecting the lowest level of UV-C back to the sensors. A set of controllers contained in the device calculates the time required to obtain a bactericidal dose of UV-C reflected back from darkest area. Once a bactericidal dose has been reflected to all the sensors, the unit shuts down.

9 Claims, 5 Drawing Sheets

ELEVATOR STERILIZATION SYSTEM AND METHOD OF USING SAME

CROSS-REFERENCE TO RELATED APPLICATION(S)

This application claims priority to U.S. Provisional Application No. 63/054,998, filed Jul. 22, 2020. This patent application is incorporated by reference herein in its entirety to provide continuity of disclosure.

FIELD OF THE INVENTION

This invention relates to methods and devices for bacterial, fungal, and/or viral sterilization, and is specifically directed to a method and device for sterilizing elevator cars.

BACKGROUND OF THE INVENTION

It is well known that infections are common, costly, and sometimes lethal. Significant morbidity, mortality, and costs are associated with infections. Many factors contribute to dangerous infections. Most notably are the overuse of antibiotics and poor personal hygiene such as hand washing. Abundant evidence also shows that the enclosed, highly trafficked environments contribute to the problem by harboring virulent strains of bacteria, fungi, and viruses, and that many methods commonly used are ineffective and may actually spread contaminants.

Attempts to eradicate surface contaminates from this setting have varied greatly in strategy and success. These have ranged from antiseptic soaps to fumigation with formaldehyde gas. Topical antiseptics are problematic for several reasons. First, they have recently been shown to actually induce antibiotic resistances and thus may be adding to the problem. Secondly, many surfaces such as buttons, television sets, and monitoring controls are difficult if not impossible to decontaminate with liquid disinfectants without harming the electronics. Gas disinfection, while effective, is time consuming, hazardous to workers, and environmentally unwise.

Ultraviolet (UV) light has been long used for disinfection and sterilization. Ultraviolet light may be produced artificially by electric-arc lamps. Recently, the widespread availability of low to medium pressure mercury bulbs has led to the development of devices which use UV-C to decontaminate water supplies. UV-C is a high frequency wavelength of light within the ultraviolet band and has been shown to be the most bactericidal type of ultraviolet light. UV-C has wavelengths of about 2800 Å to 150 Å. The only recent availability of the appropriate bulbs as well as significant safety concerns regarding worker exposure to UV-C likely contribute to the lack of efforts to use UV-C outside of self-contained water purification systems.

SUMMARY

The sanitization and sterilization device of the present invention is an automated elevator car sterilizer and sanitizer. The sanitization and sterilization may be incorporated into the elevator car design. The sanitization and sterilization device is positioned in an elevator car where concern exists regarding the presence of pathogenic bacteria on environmental surfaces or in the air. For an initial interval after actuation, motion detectors sense movement, or weight sensors sense weight or heat sensors sense heat to assure that occupants have evacuated the space to be sterilized. Subsequently, UV-C generators, such as a bank of mercury bulbs, generate intense levels of UV-C.

After the bulbs have reached a steady state of output, an array of UV-C sensors scan the elevator car and determine the darkest area, or the area reflecting the lowest level of UV-C back to the sensors. Logic contained in the device calculates the time required to obtain a bactericidal dose of UV-C reflected back from darkest area. Once a bactericidal dose has been reflected to all the sensors, the unit shuts down. By relying on reflected doses rather than direct exposure, the device is able to sterilize or sanitize all surfaces within the elevator that are within view of an exposed wall or ceiling. The pathogenic elements in the elevator have then been effectively eliminated.

BRIEF DESCRIPTION OF THE DRAWINGS

In the detailed description presented below, reference will be made to the following drawings.

DETAILED DESCRIPTION

Figure 1A:
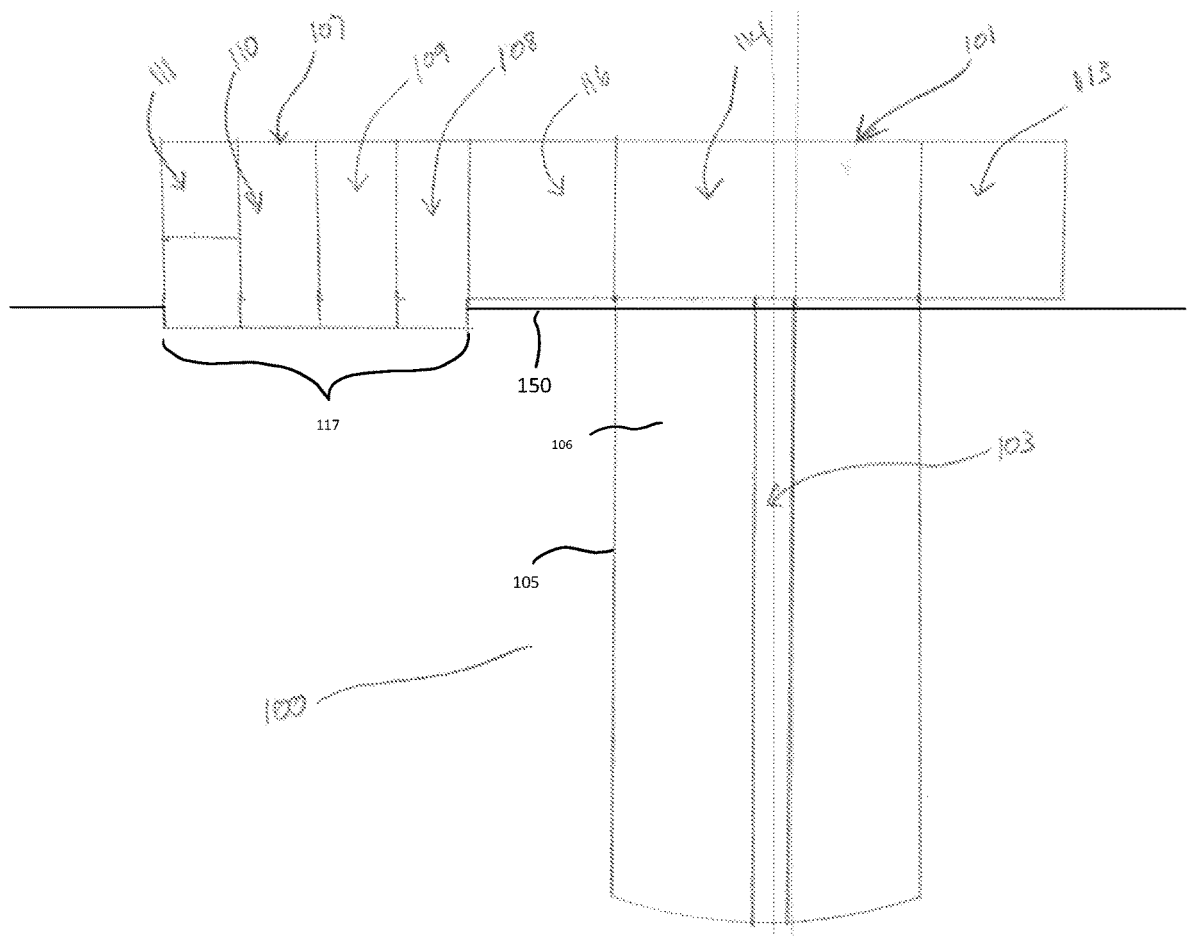
FIG. 1A is a side view of a sanitization and sterilization device of a preferred embodiment.
Figure 1B:
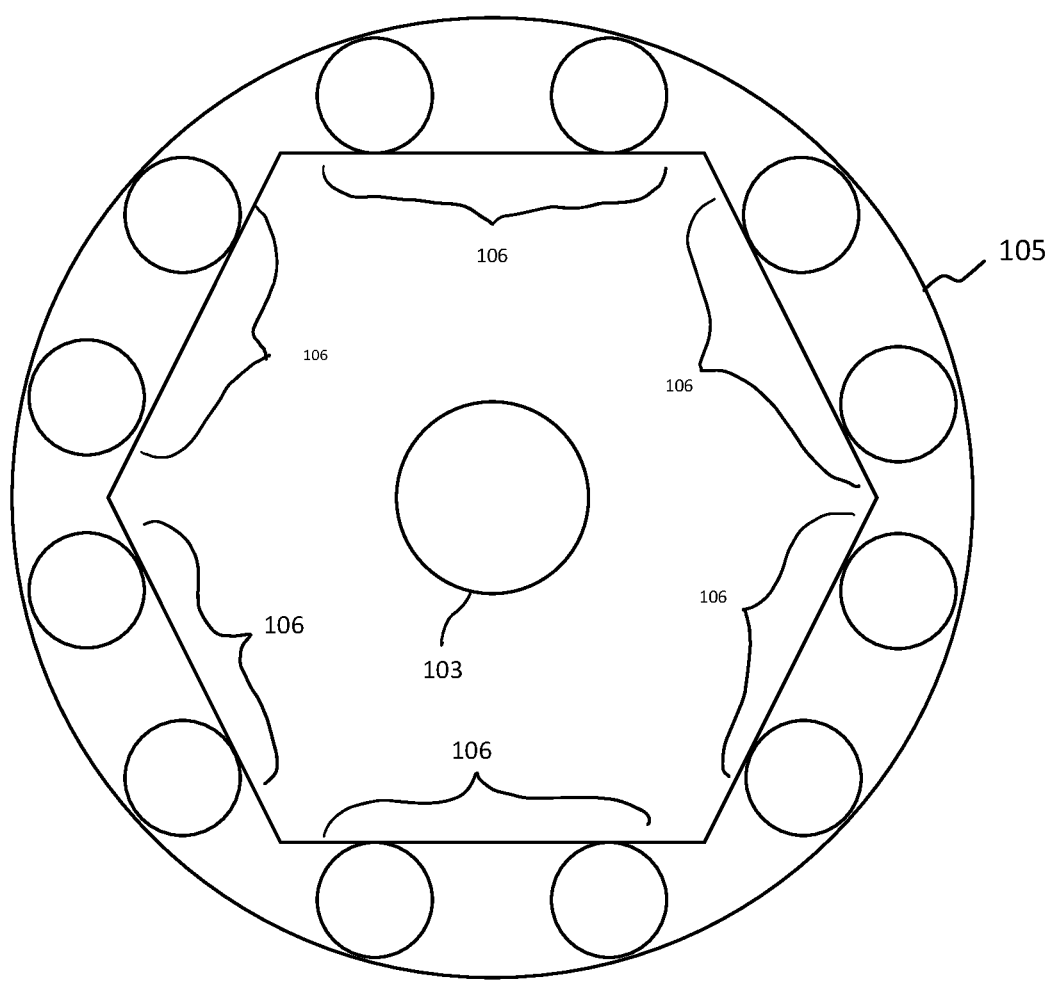
FIG. 1B is an end view of a set of a bulbs of a sanitization and sterilization device of a preferred embodiment.

Referring to FIGS. 1A and 1B, sanitization and sterilization device 100 includes base 101. Base 101 includes a set of boxes in which are housed circuits 116, power supply 113, and bulb ballasts 114. A central post 103 extends from base 101. Around central post 103 is set of UV-C emitting bulbs 105. In a preferred embodiment as shown, six pairs of medium pressure mercury bulbs 106 are preferably present (two pairs not shown), with each pair positioned equidistant from the pair on each side, such that they are present at 360° around the device. The bulbs may be 115-Watt germicidal lamps that produce 300 microwatts of ultraviolet radiation at 1 meter. Each pair of bulbs is preferred to provide not less than 80° of coverage. A control box 117 adjacent to the base 101 contains wireless components 107, the UV-C sensor array 108, a set of stamp controllers 109, occupant sensors 110, audible and visible alarms 111. In some embodiments occupant sensors 110 are motion sensors. In other embodiments, other sensors may be used, such as weight sensors (not shown) or heat sensors (not shown) may be used. In a preferred embodiment, the sanitization and sterilization device 100 is attached to the center of the ceiling 150 of the elevator car.

Figure 2:
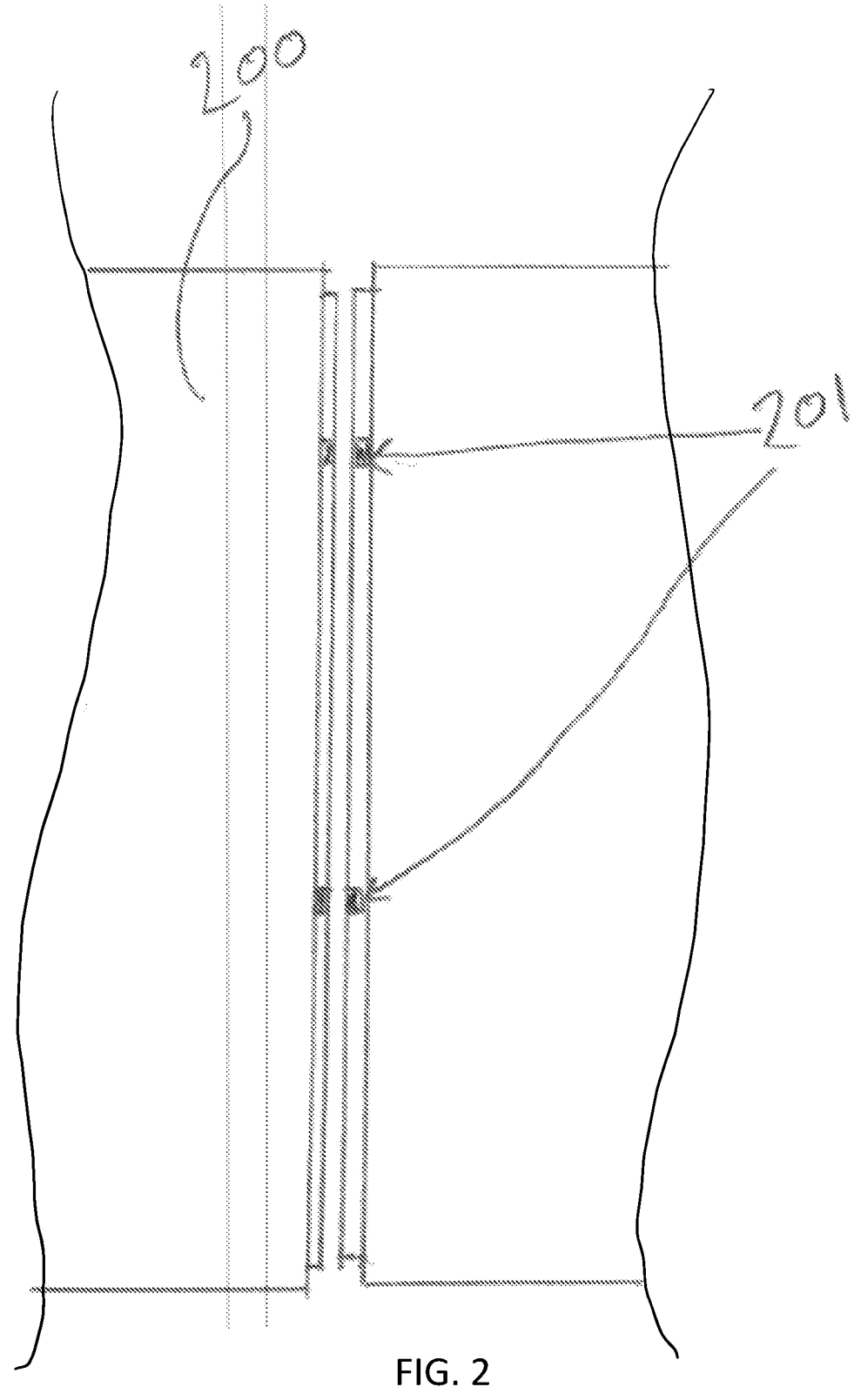
FIG. 2 is a front view of a set of sensors of a sanitization and sterilization device of a preferred embodiment.

Referring to FIG. 2, door contacts 201 are shown. These contacts are placed in doors 200 of the elevator in which the device is operating. The door contacts 201 are switches which disable the device if any one of the switches is opened, such as by opening the doors 200. The occupant sensors 110 or other sensors (not shown) are immediately activated upon activation of the device and prior to powering of the bulb ballasts 114 and the bulbs 105, by means of a time delay. If the occupant sensors 110 such as motion sensors or other sensors sense motion or an occupant at any time during the operation of the device, power to the bulb ballasts 114 and the bulbs 105 is immediately disabled. A preferred embodiment has 360° passive ultrasonic motion sensors located on the device facing into the elevator car (not shown).

Figure 3:
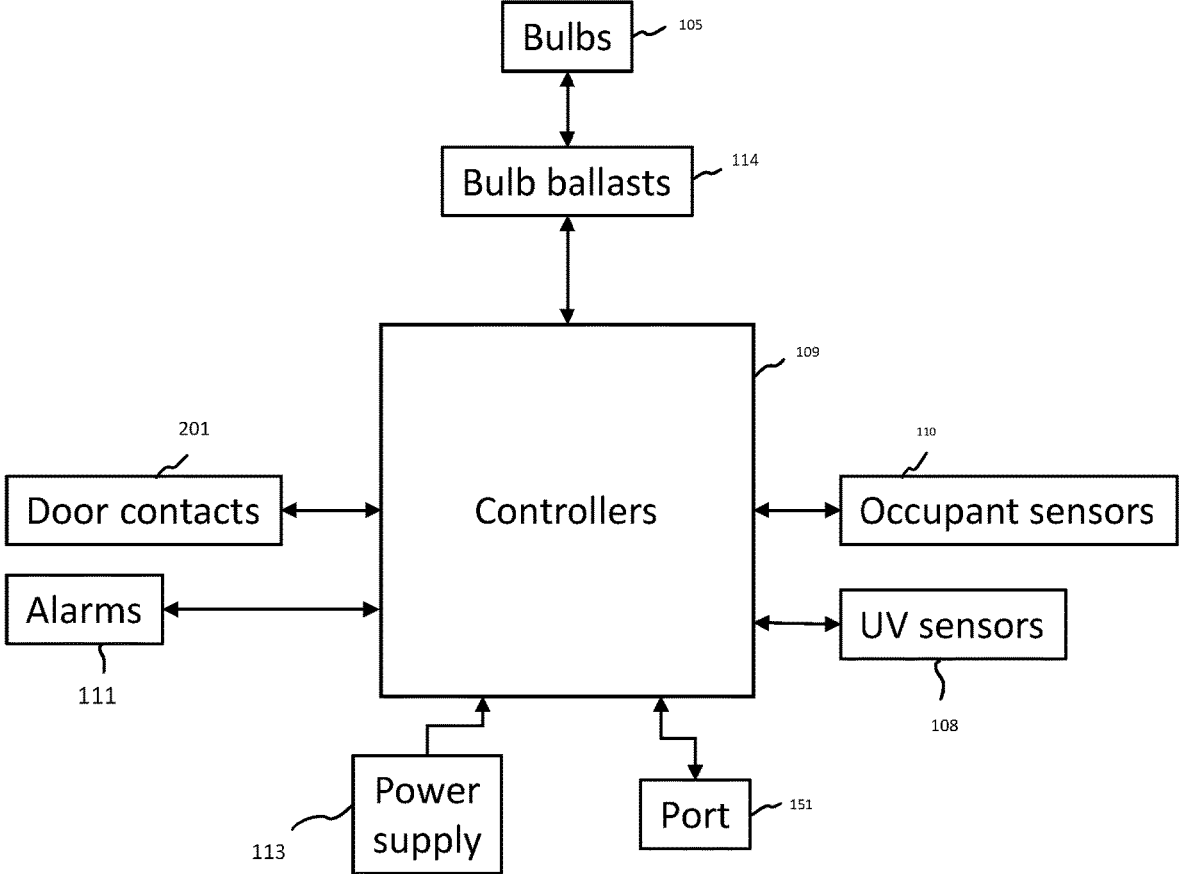
FIG. 3 is a schematic of the controls of a sanitization and sterilization device of a preferred embodiment.

Referring to FIG. 3, sanitization and sterilization device 100 is controlled by a series of programmable basic stamp controllers 109. The set of stamp controllers 109 activate set of occupant sensors 110 at least one minute prior to activation of the UV-C bulbs and continue to monitor the set of occupant sensors 110. The set of stamp controllers 109 perform all calculations regarding bactericidal doses, store cumulative dosing data, and system checks to alert a user of bulb failure. This is needed since no one can actually look at the unit to check for burned out bulbs or damaged banks. The set of stamp controllers 109 can be programmed by attaching them to a personal computer via a serial port connection 151, thus allowing alteration to the algorithms to accommodate special circumstances. Set of stamp controllers 109 are further connected to power supply 113, door contacts 201, alarms 111, and to UV-C sensor array 108. Each of bulb ballasts 114 is connected to set of stamp controllers 109. Each of bulbs 105 is connected to a bulb ballast 114.

An additional embodiment of the device provides UV-C bulbs or lamps that are placed strategically at various locations within, or directed towards, the space to be treated in the elevator car. The bulbs may be located at two or more locations in the elevator car to be treated. The bulbs may be connected to the base unit and positioned at remote locations from the base. The device in this embodiment may utilize a single bank of sensors to measure doses at locations within the area to be treated. Alternatively, multiple remote sensors, or a combination of remote and central sensors, may be provided to measure and control the dosing of UV-C to the treated area.

Figure 4:
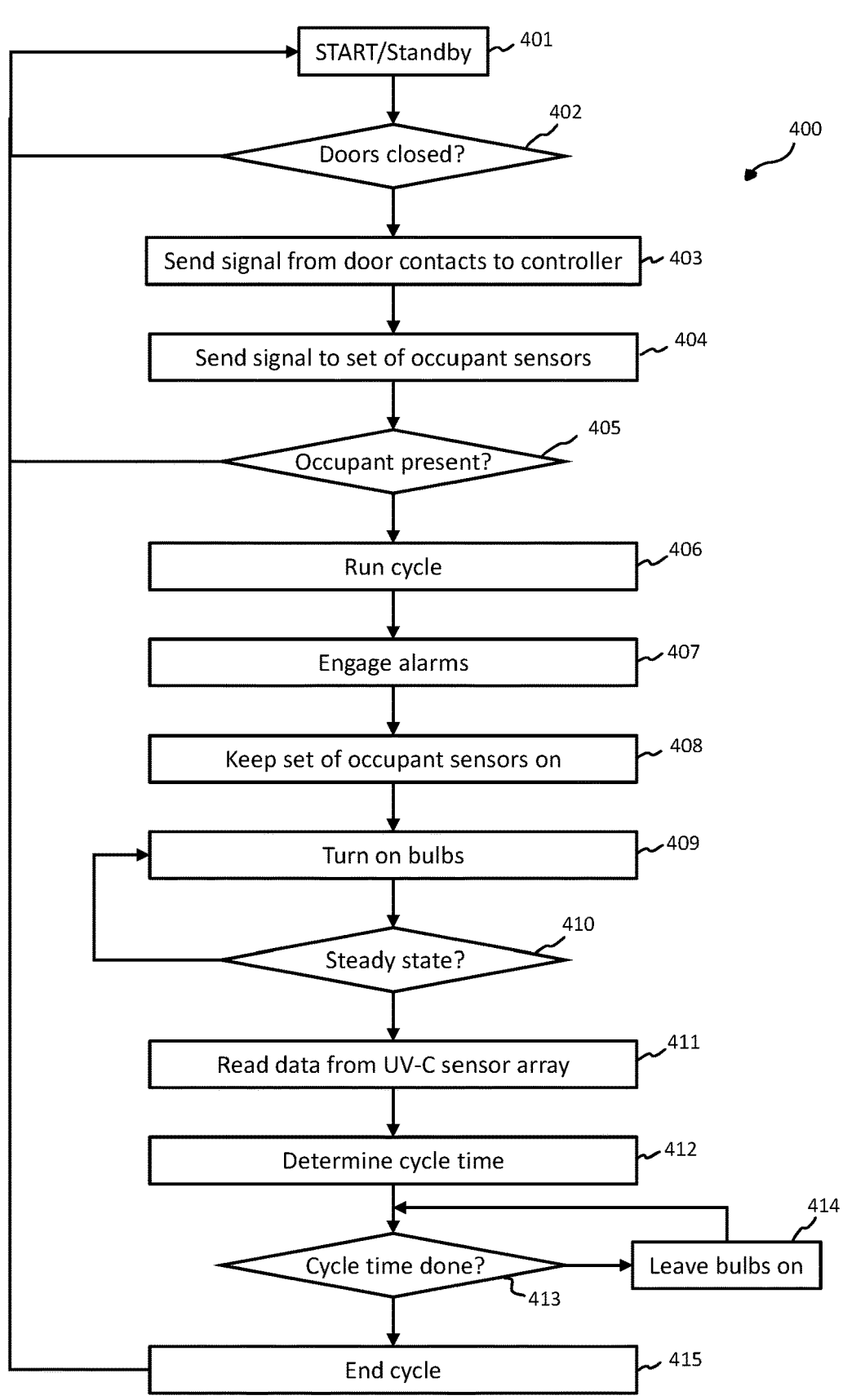
FIG. 4 is a flowchart of a method for sanitization and sterilization an elevator cart of a preferred embodiment.

Referring to FIG. 4, method 400 for using sanitization and sterilization device 100 is described, which begins at step 401 at start/standby mode of sanitization and sterilization device 100. At step 402, the door contacts determine whether the elevator doors are closed. If not, method 400 returns to step 401 in the start/standby mode. If the doors are closed, then at step 403 a set of signals is sent to the set of stamp controllers 109.

At step 404, the set of stamp controllers 109 sends a signal to the set of occupant sensors 110 (motion or otherwise) to determine if an occupant is present in the elevator at step 405. If an occupant is present, then method 400 returns to step 401 in the start/standby mode.

If no occupant is sensed, set of stamp controllers 109 initiates a sterilization cycle at step 406. At step 407, audible alarms are engaged and the set of occupant sensors 110 stays on at step 408, until the entire cycle has been complete. The set of occupant sensors 110 continuously check to see if an occupant is present. Should the set of motions sensors detect an occupant, method 400 returns to step 401 and the unit automatically deactivates itself.

At step 409, the bulbs 106 are powered on. At step 410, set of stamp controllers 109 check to see if the bulbs 106 are in a steady state. If not in a steady state, method 400 return to step 409 to remain on. At step 411, when sufficient time has elapsed to allow the bulbs 106 to reach a steady state output (one minute or less), the set of stamp controllers 109 reads data from all the individual sensors located on UV-C sensor array 108. UV-C sensor array 108 senses 360 degrees at a minimum with overlapping of their window of view. Each sensor of UV-C sensor array 108 is oriented away from the device, thus measuring the dose of UV-C reflected back to the unit. This data is fed into the set of stamp controllers 109 where it is integrated to compute cumulative exposure of UV-C reflected back from each sensor in UV-C sensor array 108.

At step 412, the set of stamp controllers 109 determines the sanitization or sterilization cycle time bulbs 106 will need to stay activated to allow a bactericidal dose of UV-C to be reflected back to the unit from all directions based on the least reflective surface or direction (of several thousand "snapshots"). At step 413, the set of stamp controllers 109 determines whether the sanitization or sterilization cycle time is complete. If not, bulbs 106 remain on at step 414 and method 400 returns to step 413.

Once the sanitization or sterilization cycle time has elapsed, which is a sufficient time for a lethal dose of UV-C to be reflected back to the unit, then the set of stamp controllers 109 powers down the bulbs and the sanitization or sterilization cycle ends at step 415 and method 400 returns to the start/standby state.

Upon completion of the cycle, sanitization and sterilization device 100 has sanitized or sterilized all the exposed surfaces within the elevator car, including the primary shadows such as those caused by any rails.

In a preferred embodiment, at direct exposure from approximately two meters, sanitization and sterilization device 100 is able to sanitize and reduce colony counts of common hospital pathogens by a minimum of 99.9% in approximately one minute and achieve sterilization in approximately 10 minutes. Through the use of paint that reflects 50-85% of the UV-C in the elevator car, the efficiency of sanitization and sterilization device 100 is increased, allowing for decreased exposure times. In most environments, there is a presence of what microbiology labs label as "wild spore forms" of bacteria. These bacteria are not known to cause human disease, and yet, are resistant to low doses of UV-C. The dual programming modes of sanitization and sterilization device 100 allow treatment as required. One mode (Sanitize) kills all known pathogens and requires a lower exposure and thus shorter time. The other mode (Sterilize) kills all species of bacteria and requires greater cumulative doses and therefore more time. By relying on reflected doses rather than direct exposure, the sanitization and sterilization device 100 is able to sterilize or sanitize all surfaces within the car.

In a preferred embodiment, sanitization and sterilization device 100 self-monitors bactericidal levels. Reflected doses of UV-C are measured by UV-C sensor array 108, and sanitization and sterilization device 100 remains activated until bactericidal levels are received beyond a predetermined threshold. This ensures that areas in relative shadow and not in direct line of sight with sanitization and sterilization device 100 are sterilized.

Without adequate safety features, daily use of intense UV-C is dangerous and impractical. To overcome this, sanitization and sterilization device 100 has occupant sensors 110 that assure the car is vacant of personnel prior to activation. Hard wired plugs on sanitization and sterilization device 100 are available for additional door or other entry monitoring devices special situation may dictate. Once activated, sanitization and sterilization device 100 shuts down instantly when motion occurs anywhere in the car being sterilized or when an occupant is otherwise sensed.

Sanitization and sterilization device 100 is able to sanitize or sterilize all exposed surfaces in an elevator. Sanitization and sterilization device 100 is able to do so safely, leave no residual toxins or radiation, and generates no adverse environmental side products. In addition, sanitization and sterilization device 100 is able to notify, via alarms 111 generating a visual and/or audible pattern, the user of the time required to perform this task and automatically shuts down upon completion of sterilization. Highly reflective paints are beneficial to the method of area sterilization disclosed herein.

It will be appreciated by those skilled in the art that modifications can be made to the embodiments disclosed and remain within the inventive concept. Therefore, this invention is not limited to the specific embodiments disclosed, but is intended to cover changes within the scope and spirit of the claims.

The invention claimed is:

1. A dual-mode anti-pathogenic elevator car comprising:
an elevator floor;
a set of elevator walls connected to the elevator floor;
an elevator ceiling connected to the set elevator walls;
a set of elevator doors connected to the set of elevator walls;
an anti-pathogen device connected to the elevator ceiling comprising:
  a base connected to the elevator ceiling;
  a post connected to the base;
  a set of UV-C bulbs connected to the post and surrounding the post;
  a set of controllers connected to the set of UV-C bulbs;
  a sensor array connected to the set of controllers;

a set of occupant sensors connected to the set of controllers;
  a set of alarms connected to the set of controllers; and,
  a set of door contacts connected to the set of controllers and to the set of elevator doors.

2. The dual-mode anti-pathogen elevator car of claim 1, further comprising a set of rails connected to the set of elevator walls.

3. The dual-mode anti-pathogen elevator car of claim 1, wherein the set of UV-C bulbs has an exposure time.

4. The dual-mode anti-pathogen elevator car of claim 3, wherein the exposure time is set to a sterilization time.

5. The dual-mode anti-pathogen elevator car of claim 3, wherein the exposure time is set to a sanitization time.

6. The dual-mode anti-pathogen elevator car of claim 1, wherein the set of elevator walls comprises UV-C reflective paint.

7. The dual-mode anti-pathogen elevator car of claim 1, wherein the set of occupant sensors is a set of motion sensors.

8. The dual-mode anti-pathogen elevator car of claim 1, wherein the set of occupant sensors is a set of weight sensors.

9. The dual-mode anti-pathogen elevator car of claim 1, wherein the set of occupant sensors is a set of heat sensors.

\* \* \* \* \*